Sept. 8, 1964 A. MEILLAND Plant Pat. 2,444
ROSE PLANT
Filed Oct. 21, 1963
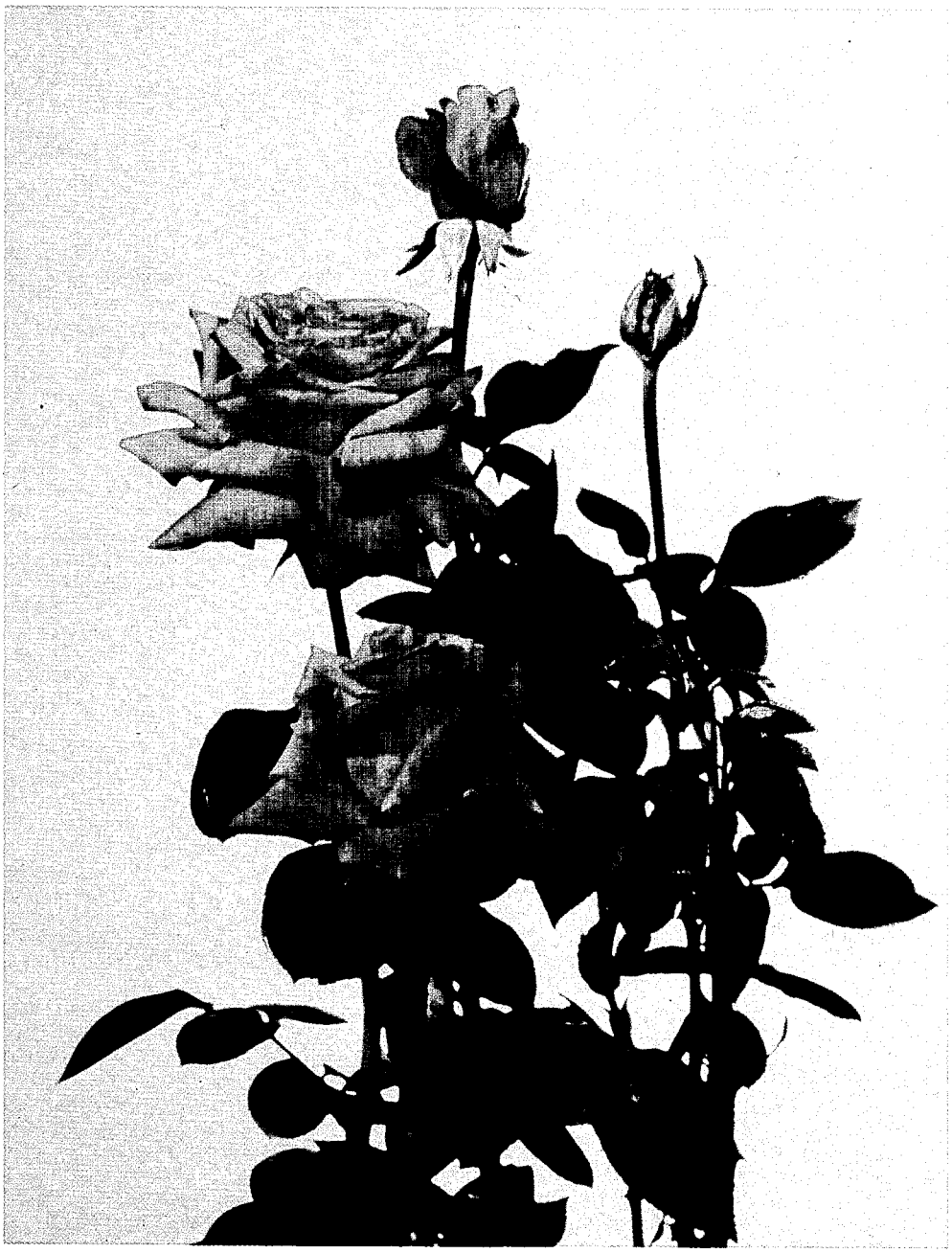
Inventor.
Alain Meilland
By: Robb & Robb
Attorneys.

United States Patent Office

Plant Pat. 2,444
Patented Sept. 8, 1964

2,444
ROSE PLANT

Alain Meilland, Cap d'Antibes, Alpes Maritimes, France, assignor to The Conard-Pyle Company, West Grove, Pa., a corporation of Pennsylvania Filed Oct. 21, 1963, Ser. No. 317,856
1 Claim. (Cl. Plt.—11)

The present invention relates to a new and distinct variety of rose plant of the hybrid tea class, which was originated by me by crossing an unnamed and unpatented seedling derived from a cross of "Independence" (U.S. Plant Patent No. 1,036, known in Germany as "Kordes' Sondermeldung")×"Happiness" (U.S. Plant Patent No. 911, known in France as "Rouge Meilland") with the variety "Peace" (U.S. Plant Patent No. 591, known in France as "Mme. A. Meilland").

As the result of this breeding, I have produced a new and improved rose variety which is evidenced by the following unique combination of characteristics which are outstanding therein and which distinguish the new variety from its parents, as well as from all other varieties of which I am aware:

(1) A vigorous and upright habit of growth;

(2) A habit of bearing flowers singly on long stems of good length for cut flowers;

(3) A high-centered flower form, with the flowers being of good petalage, usually ranging from 45 to 55 petals, which make the flowers of good exhibition form;

(4) A distinctive and attractive general color tonality of the flowers varying from Rose Pink to Rose Red, with a darker purplish margin around the petals which become more pronounced in hot, sunny weather; and (5) A slight to moderate tea fragrance of the flowers.

In comparison with its unnamed seedling parent, the new variety produces flowers of superior form, and the flowers have a much greater variability in color than those of this parent.

As compared with its pollen parent "Peace," the new variety has a taller growth and the flowering canes are considerably longer; in their mature form, the flowers are high-centered in contrast to the more cupped, high-centered and globular form of the flowers of this parent; and the flowers have a totally different color, being generally Rose Red in contrast to the yellow coloration of the flowers of "Peace."

Asexual reproduction of the new variety by budding, as performed in France, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hydrid tea.

Breeding: Seedling.

*Seed parent.*—An unnamed seedling of "Independence"×"Happiness."

*Pollen parent.*—"Peace."

Propagation: Holds its distinguishing characteristics through succeeding propagations by budding.

*Flower.*

Locality where grown and observed: West Grove, Pennsylvania, U.S.A.

Flowers borne: Singly to stem; on long and strong stems.

Quantity of bloom: Free, outdoors.

Continuity: Continuous.

Fragrance: From slight to moderate. Nature—tea.

Bud:

*Peduncle.*—Medium length; medium caliper; erect, stiff; rough; with medium number of brown prickles. Color—Lettuce Green, Plate 861/1, overlaid with Oxblood Red, Plate 00823/3.

*Before calyx breaks.*—Size—medium. Form—pointed-ovoid; with a conspicuous neck; with foliaceous appendages on the surface of the bud; with medium slender foliaceous parts extending beyond the tip of the bud equal to ¼ or more of its length.

*As calyx breaks.*—Color—Maroon, Plate 1030, shaded with black.

*As first petal opens.*—Size—medium. Form—medium length; pointed. Color: outside—Rose Red, Plate 724/3, shaded with Purple Madder, Plate 1028 where first exposed to light; inside—Rose Bengal, Plate 25.

*Opening.*—Opens up well.

Bloom:

*Size (when fully open).*—Large; from 3½ inches to 4 inches.

*Petalage.*—Very double; from 45 to 55 petals; arranged regularly.

*Form.*—High-centered at first and remaining high-centered; petals being at first loosely rolled outward and remaining loosely rolled outward at maturity.

Petals:

*Texture.*—Medium thickness; leathery.

*Appearance.*—Inside—satiny. Outside—velvety.

*Shape.*—Outer petals—round. Intermediate petals—round. Inner petals—undulate.

This description of a newly opened flower was made from a rose grown outdoors during the month of September at West Grove, Pennsylvania, U.S.A.:

*Color.*—Outer petal: outside surface—Solferino Purple, Plate 26/1, irregularly shaded with Ruby Red, Plate 827/1 over upper half of petal, with point of attachment Uranium Green, Plate 63/2; inside surface—Tyrian Purple, Plate 727/2, often broadly margined over upper half of petal with Dahlia Purple, Plate 931/1, becoming tinted with Fuchsine Pink, Plate 627/1 over basal ¼ of petal, and with point of attachment Uranium Green, Plate 63/2. Intermediate petal: outside surface—Solferino Purple, Plate 26/1, margined with Solferino Purple, Plate 26/2, and with point of attachment Uranium Green, Plate 63/2; inside surface—Solferino Purple, Plate 26/1, with point of attachment Uranium Green, Plate 63/2. Inner petal: outside surface—Solferino Purple, Plate 26/2, with point of attachment Uranium Green, Plate 63/2; inside surface—between Solferino Purple, Plate 26/1 and Solferino Purple, Plate 26/2, with point of attachment Uranium Green, Plate 63/2.

This description was made from a rose that was open for three days outdoors during the month of September at West Grove, Pennsylvania, U.S.A.:

*Color.*—Outer petal: outside surface—Solferino Purple, Plate 26 over upper half of petal, grading to Solferino Purple, Plate 26/2, with point of attachment Primrose Yellow, Plate 601/3; inside surface—Solferino Purple, Plate 26/1, often broadly margined with near Dahlia Purple, Plate 931/1, grading to Solferino Purple, Plate 26/2 over basal half of petal, with base of petal and point of attachment Primrose Yellow, Plate 601/3. Inner petal: outside surface—near Solferino Purple, Plate 26/2, often with a stripe of near white running from point of attachment to apex of petal, with point of attachment Primrose Yellow, Plate 601/2; inside surface—Solferino Purple, Plate 26/2, usually shaded over upper half of petal with Solferino Purple, Plate 26, with point of attachment Primrose Yellow, Plate 601/2.

*General color effect.*—Newly opened flower—Solferino Purple, Plate 26/1, with outer petals often heavily shaded with Dahlia Purple, Plate 931/1. 3-days open—Solferino Purple, Plate 26/1, with outer margins of outer petals showing Dahlia Purple, Plate 931/1.

*Behavier.*—Drop off cleanly; dark margins of petals become more accentuated during hot weather.

*Flower longevity.*—On bush in garden—4 days in September. Cut roses grown outdoors and kept at living-room temperatures—5 days in September.

*Reproductive Organs*

Stamens: Many; arranged irregularly about pistils; mixed with petaloids.

Filaments: Many; medium length; most with anthers. Color—Coral Pink, Plate 0619, grading to Canary Yellow, Plate 2/2 at base.

Anthers: Open at various times; medium size; occasionally an anther fused with a petaloid. Color—Aureolin, Plate 3.

Pollen: Abundant quantity. Color—gold.

Pistils: Medium number.

Styles: Uneven; medium length; medium caliper; bunched.

Stigma: Color—white-yellow.

Ovaries: Some protruding from receptacle.

Hips: None observed.

Sepals: Permanent; medium length; spear-shaped.

Seeds: None observed.

*Plant*

Foliage:

*Leaves.*—Compound of 3, 5 or 7 leaflets; normal abundance; moderately large; leathery.

*Leaflets.*—Shape—oval. Apex—acuminate. Base—obtuse. Margin—simply serrate.

*Color.*—Mature: upper surface—Ivy Green, Plate 0001060/1; under surface—Willow Green, Plate 000862/1. Young: upper surface — Parsley Green, Plate 00962/3, lightly overlaid with Oxblood Red, Plate 00823/3; under surface—Parsley Green, Plate 00962/3, overlaid with Garnet Brown, Plate 00918/3.

*Rachis (the supporting stem of the compound leaf).*—Medium caliper. Upper side—grooved; hairy. Under side—sparsley prickly.

*Stipules.*—Medium length; medium width; with points of medium length turning out at an angle of more than 45°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Vigorous.

*Canes.*—Moderately heavy.

*Main stems.* — Dull. Color — Fern Green, Plate 0862. Prickles—several; color—brown. Hairs—none.

*Branches.* — Dull. Color — Parsley Green, Plate 0962/3, often overlaid with near Erythrite Red, Plate 0027/1. Prickles—several; color—reddish brown. Hairs—none.

*New shoots.*—Dull. Color—near Fern Green, Plate 0862/1, overlaid with near Pansy Purple, Plate 928/2. Prickles — several; color — reddish. Hairs—none.

I claim:

A new and distinct variety of rose plant of the hybrid tea class, substantially as herein shown and described, characterized particularly as to novelty by the unique combination of a vigorous and upright habit of growth, a habit of producing the flowers singly on long stems of good cutting length, high-centered flowers of good petal-age with consequent good exhibition form, a distinctive and attractive general color tonality of the flowers varying from Rose Pink to Rose Red, with a darker purplish margin about the petals which becomes more pronounced in hot, sunny weather, and a slight to moderate tea fragrance of the flowers.

No references cited.